United States Patent
Yan et al.

(10) Patent No.: US 10,877,022 B1
(45) Date of Patent: Dec. 29, 2020

(54) OCCULT BLOOD TESTING DEVICE

(71) Applicant: TAIWAN REDEYE BIOMEDICAL INC., Hsinchu (TW)

(72) Inventors: Shuo-Ting Yan, Hsinchu (TW); Tsung-Jui Lin, Hsinchu (TW); I-Hua Wang, Hsinchu (TW)

(73) Assignee: Taiwan Redeye Biomedical Inc., Hsinchu (TW)

( * ) Notice: Subject to any disclaimer, the term of this patent is extended or adjusted under 35 U.S.C. 154(b) by 0 days.

(21) Appl. No.: 16/790,916

(22) Filed: Feb. 14, 2020

(51) Int. Cl.
| | |
|---|---|
| *G01N 33/49* | (2006.01) |
| *G01N 21/25* | (2006.01) |
| *G01N 21/59* | (2006.01) |
| *G01N 21/01* | (2006.01) |

(52) U.S. Cl.
CPC ............. *G01N 33/49* (2013.01); *G01N 21/01* (2013.01); *G01N 21/253* (2013.01); *G01N 21/59* (2013.01); *G01N 2021/0112* (2013.01); *G01N 2201/0415* (2013.01); *G01N 2201/0626* (2013.01)

(58) Field of Classification Search
CPC ...... G01N 33/49; G01N 21/01; G01N 21/253; G01N 21/59; G01N 2021/0112; G01N 2201/0415; G01N 2201/0626
USPC .......................................................... 356/39
See application file for complete search history.

(56) References Cited

U.S. PATENT DOCUMENTS

| | | | |
|---|---|---|---|
| 9,566,027 B2* | 2/2017 | Tamir | A61B 5/157 |
| 10,746,652 B1* | 8/2020 | Yan | G01N 21/31 |
| 10,761,015 B1* | 9/2020 | Yan | G01N 21/3103 |
| 2010/0261988 A1* | 10/2010 | Tamir | A61B 5/150114 600/365 |
| 2017/0181682 A1* | 6/2017 | Tamir | A61B 5/150114 |
| 2017/0212039 A1* | 7/2017 | Yan | G01J 3/10 |
| 2018/0085098 A1* | 3/2018 | Attar | G01N 33/493 |
| 2019/0265134 A1* | 8/2019 | Ivosevic | A61B 5/150213 |
| 2019/0323949 A1* | 10/2019 | Carvalho Sousa | G01N 21/255 |

* cited by examiner

*Primary Examiner* — Roy M Punnoose
(74) *Attorney, Agent, or Firm* — Rosenberg, Klein & Lee

(57) ABSTRACT

An occult blood testing device is disclosed. The occult blood testing device includes a main body, a plurality of ribs, at least one light emitting unit, and at least one light sensing unit, wherein the ribs are disposed on an outer surface of the main body, and the light emitting unit and the light sensing unit are disposed in an accommodation space of the main body. The light emitting unit emits an incident light beam and aims the incident light beam towards a direction of an open end of the main body at a test solution, and the light sensing unit receives a detection light beam formed by the incident light beam that penetrated the test solution. When a filter unit is sleeved over the main body, a part of the filter unit is supported by the ribs and a gap is formed between the filter unit and the outer surface of the main body. Through the gap, gas in the accommodation space of the main body can be expelled to prevent the gas existence from affecting the accuracy of the occult blood test.

13 Claims, 7 Drawing Sheets

OCCULT BLOOD TESTING DEVICE

FIELD OF THE INVENTION

The invention relates to an occult blood testing device, more particularly, to a fecal occult blood testing device with better test accuracy and is convenient for user to use and clean.

BACKGROUND

With the changes in people's diet and life habits, colorectal cancer has become one of the most common cancer types diagnosed. In Taiwan, colon cancer rate has topped the cancer ranking for more than a decade and is also the highest in the world. The incidence rate and death rate of colon cancer patients are respectively 18.6% and 20.1% in China, which both topped the rankings in the world. The incidence rate for colon cancer is 8% out of all cancer patients, which ranks among the top few spots in USA.

Testing for fecal occult blood is one of the methods to detect colon cancer at early stage. Conventional stool occult blood test requires collecting fecal specimen, sending it to the hospital for testing and waiting for the test result, which not only is inconvenient for the patient, the inability of testing-at-anytime also prohibits self-management of the patient for long-term health monitoring.

Moreover, the specimen collected for conventional testing is about 1 gram, but only 6 milligrams is used by the medical unit for testing. However, occult blood in the stool is not distributed evenly and so false negative result is easily concluded from the testing when the occult blood was not collected in the specimen. In addition, the bleeding of tumor or polyp is periodic, not continuous, and so it is possible that the tumor or the polyp did not bleed on the day of or the day before the collection of stool specimen, causing the test result to be false negative. Hence, improving the accuracy and convenience of stool occult blood test is an important factor for early diagnosis and treatment of colon cancer to lower the death rate.

SUMMARY

An objective of the invention is to provide an occult blood testing device that is convenient for user to clean after taking the test and is capable of preventing solid residues in the test solution from contaminating the testing device or the user.

Another objective of the invention is to provide an occult blood testing device having a main body with a plurality of ribs disposed on the outer surface thereof. When a filter unit is sleeved over the main body, a gap is formed between the filter unit and the outer surface of the main body, such that gas in an accommodation space of the main body can be expelled through the gap. Thus, the number of times which the incident light beam and detection light beam are required to penetrate through gas and liquid during the test is reduced and the test accuracy is therefore improved.

To achieve the objectives mentioned above, the present invention provides an occult blood testing device, which includes a main body, a plurality of ribs, at least one light emitting unit for emitting at least one incident light beam, and at least one light sensing unit for receiving at least one detection light beam. The main body is hollow and has an open end, an accommodation space in fluid communication with the open end, and a tail end. The ribs are disposed on an outer surface of the main body along a direction from the open end to the tail end of the main body. The light emitting unit and the light sensing unit are disposed in the accommodation space of the main body. The incident light beam is aimed towards a direction of the open end and at a test solution, and the detection light beam is formed by the incident light beam that has penetrated the test solution.

The present invention further provides an occult blood testing device, which includes a main body, a plurality of rib sets, at least one light emitting unit for emitting at least one incident light beam, and at least one light sensing unit for receiving at least one detection light beam. The main body is hollow and has an open end, an accommodation space in fluid communication with the open end, and a tail end. The plurality of rib sets are disposed on an outer surface of the main body, wherein each rib set includes a plurality of ribs, and the ribs are disposed along a direction from the open end to the tail end. The light emitting unit and the light sensing unit are disposed in the accommodation space of the main body. The incident light beam is aimed towards a direction of the open end and at a test solution, and the detection light beam is formed by the incident light beam that has been penetrated the test solution.

BRIEF DESCRIPTION OF THE DRAWINGS

The structure as well as preferred modes of use, further objects, and advantages of this invention will be best understood by referring to the following detailed description of some illustrative embodiments in conjunction with the accompanying drawings, in which.

DETAILED DESCRIPTION OF THE PREFERRED EMBODIMENTS

The term "excreta" or "fecal" in the invention refers to solution excreted or produced directly by human or animal, liquid of the solution, or solution of other solvent; for example, solution in the toilet with excreta such as feces, urine, and/or phlegm therein. The term "occult blood" refers to human or animal blood in the excreta, especially blood that is invisible to human eyes.

Figure 1:
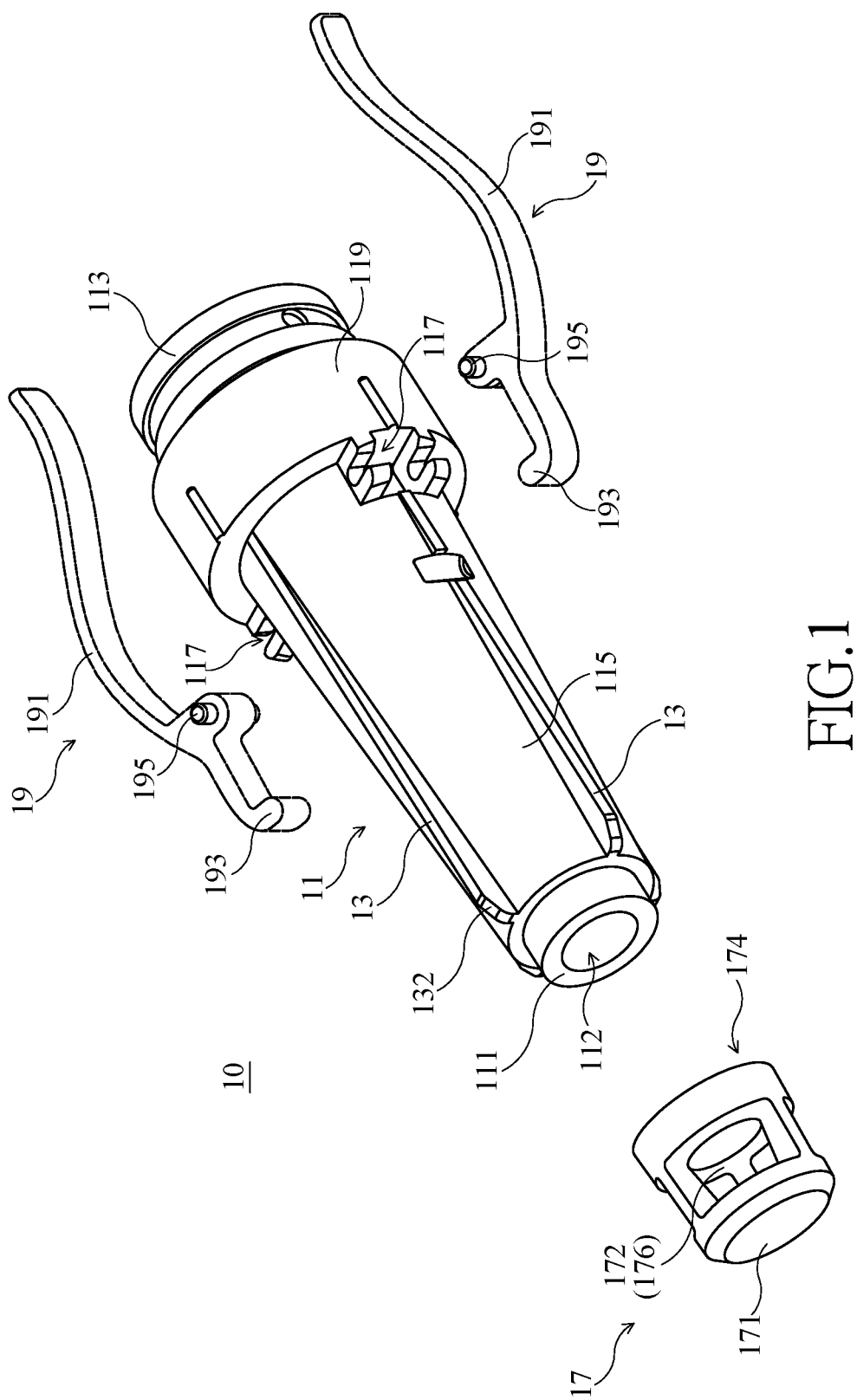
FIG. 1 is an exploded view of an occult blood testing device according to an embodiment of the invention.
Figure 2:
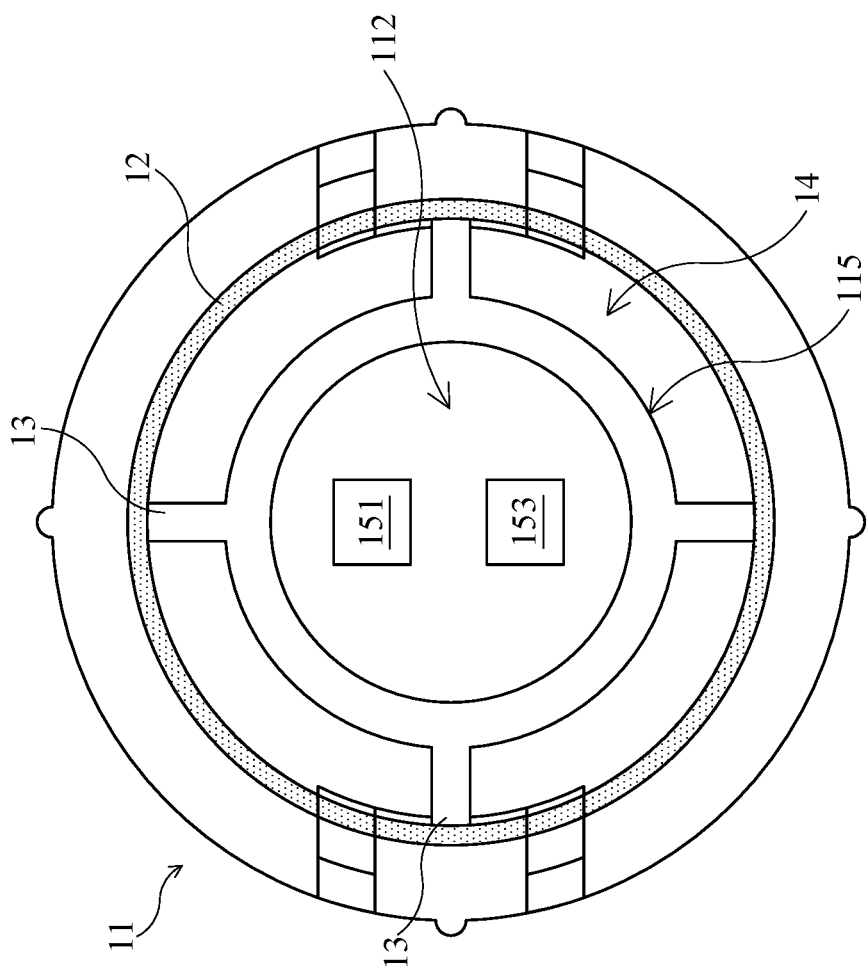
FIG. 2 is a side view, taken from an open end, of an occult blood testing device according to an embodiment of the invention.

FIGS. 1 and 2 are, respectively, an exploded view and a side view of an occult blood testing device according to an embodiment of the invention. The occult blood testing device 10, such as a fecal occult blood testing device, includes a main body 11, a plurality of ribs 13, at least one light emitting unit 151, and at least one light sensing unit 153, wherein the occult blood testing device 10 detects whether blood exists in excreta like fecal, feces, urine and/or phlegm through optical mechanism.

The main body may be hollow or cylindrical and includes an open end 111, a tail end 113, and an accommodation space 112, wherein the open end 111 is in fluid communication with the accommodation space 112. The light emitting unit 151 and the light sensing unit 153 are disposed in the accommodation space 112 of the main body 11, wherein the light emitting unit 151 is used to emit at least one incident light beam aimed towards the direction of the open end 111. The light emitting unit 151 and the light sensing unit 153 are, for example, disposed on a circuit board that is disposed in the accommodation space 112.

In one embodiment of the invention, the open end 111 of the main body 11 is connected to/attached with a probe unit 17. The probe unit 17 includes a base 171, a connect end 174, a test space 176, and at least one through hole 172, wherein the connect end 174 and the through hole 172 are in fluid communication with the test space 176, and the connect end 174 and the base 171 are opposite to and/or face each other. The probe unit 17 is connected to the open end 111 of the main body 11 via the connect end 174 to put the test space 176 in fluid communication with the accommodation space 112 and to place the base 171 of the probe unit 17 facing the open end 111 of the main body 11, such that the incident light beam emitted from the light emitting unit 151 is aimed towards the base 171 of the probe unit 17.

In particular, the probe unit 17 is barrel-shaped or cylinder-shaped, wherein the through hole 172 of the probe unit 17 is disposed on a side surface, and the connect end 174 and the base 171 are respectively disposed at two ends of the probe unit 17 and face each other. The connect end 174 of the probe unit 17 is an opening that can be sleeved over the open end 111 of the main body 11.

When using the occult blood testing device 10, the probe unit 17 and a part of the main body 11 are inserted into the test solution and the test solution enters the test space 176 of the probe unit 17 and/or the accommodation space 12 of the main body 11 via the through hole 172 of the probe unit 17. The incident light beam emitted by the light emitting unit 151 is aimed at the test solution in the test space 176 of the probe unit 17 and the incident light beam that penetrated the test solution forms at least one detection light beam.

The light sensing unit 153 of the occult blood testing device 10 is used to receive the detection light beam and transform the received detection light beam into digital signal. The light sensing unit 153 then transmits the digital signal to a processor for analysis to determine whether blood exists in the test solution.

The aforementioned embodiment is described with the main body 11 being connected to the probe unit 17, but the probe unit 17 is not an essential component of the present invention. Basically, to complete the test, the occult blood testing device 10 just needs to have the main body 11 with the open end 111 in fluid communication with the accommodation space 112 such that the incident light beam emitted by the light emitting unit 151 is aimed at the test solution in the accommodation space and that the light sensing unit 153 receives the detection light beam formed through the test solution in the accommodation space 112.

When the main body 11 is connected to the probe unit 17, the detection light beam is scattered or reflected by the base 171 of the probe unit 17, which is beneficial for the light sensing unit 153 to receive the detection light beam and the test accuracy is improved. Moreover, in the aforementioned embodiment, the main body 11 and the probe unit 17 are two separate components, but in practice, the main body 11 and the probe unit 17 can be integrated into a single component.

Although the occult blood testing device 10 is able to complete the testing through the abovementioned steps, the test solution often contains solid residues and after the test solution has been in the test space 176 of the probe unit 17 and/or the accommodation space 112 of the main body 11, the solid residue may remain in the probe unit 17 and/or the main body 11 and contaminate them.

In order to avoid the aforementioned contamination, a filter unit 12 is usually disposed on the outer surface of the main body 11 and the probe unit 17. The filter unit 12 is, for example, filter paper that is capable of filtering the solid residue in the test solution and preventing the solid residue of the test solution from coming in contact with the occult blood testing device 10. Furthermore, after the test, the user just needs to remove the filter unit 12 that is sleeved over the main body 11 and the probe unit 17 and rinse/wash the occult blood device 10 with running water to complete the cleaning of the occult blood device 10.

In general, after placing the filter unit 12 on the occult blood testing device 10 and inserting the occult blood testing device 10 with the sleeved filter unit 12 into the test solution, the filter unit 12 that is in contact with the test solution sticks tightly to the outer surface 115 of the main body 11, which causes gas that exists in the accommodation space 112 of the main body 11 and/or the test space 176 of the probe unit 17 unable to be expelled.

When the light emitting unit 151 aims the incident light beam at the test solution or when the light sensing unit 153 receives the detection light beam from the test solution, the incident light beam and/or the detection light beam may penetrate through gas and liquid many times, which creates multiple reflections and refractions and affects the test accuracy.

Hence, the occult blood testing device 10 of the invention further includes a plurality of ribs 13 disposed on the outer surface 115 of the main body 11, wherein the ribs 13 protrude from the outer surface 115 of the main body 11 and are disposed along a direction from the open end 111 to the tail end 113 of the main body 11. At least one gap 14 is formed between the filter unit 12 sleeved over the main body 11 and the outer surface 115 of the main body 11, and the gas that was in the accommodation space 112 of the main body 11 and/or the test space 176 of the probe unit 17 can be expelled through the gap 14.

In one embodiment of the invention, the main body 11 is a cylinder or a truncated cone, for example, the area of the open end 111 of the main body 11 is smaller than the area of the tail end 113 to form the truncated-cone main body 11. An axial direction and a plurality of radial directions can be defined on the main body 11, wherein each of the ribs 13 is disposed on the outer surface 115 of the main body 11 along the axial direction and protrudes from the outer surface 115 of the main body 11 along the radial direction. In addition, the included angle between any two adjacent ribs 13 of the plurality of ribs 13 is the same and therefore the outer surface 115 of the main body 11 is divided into equal sections by the plurality of ribs 13.

The number of ribs 13 is four in this embodiment as shown in FIG. 2, wherein the included angle between two adjacent ribs 13 on the main body 11 is approximately 90 degrees, and the outer surface 115 of the main body 11 is divided into four equal sections.

Figure 3:
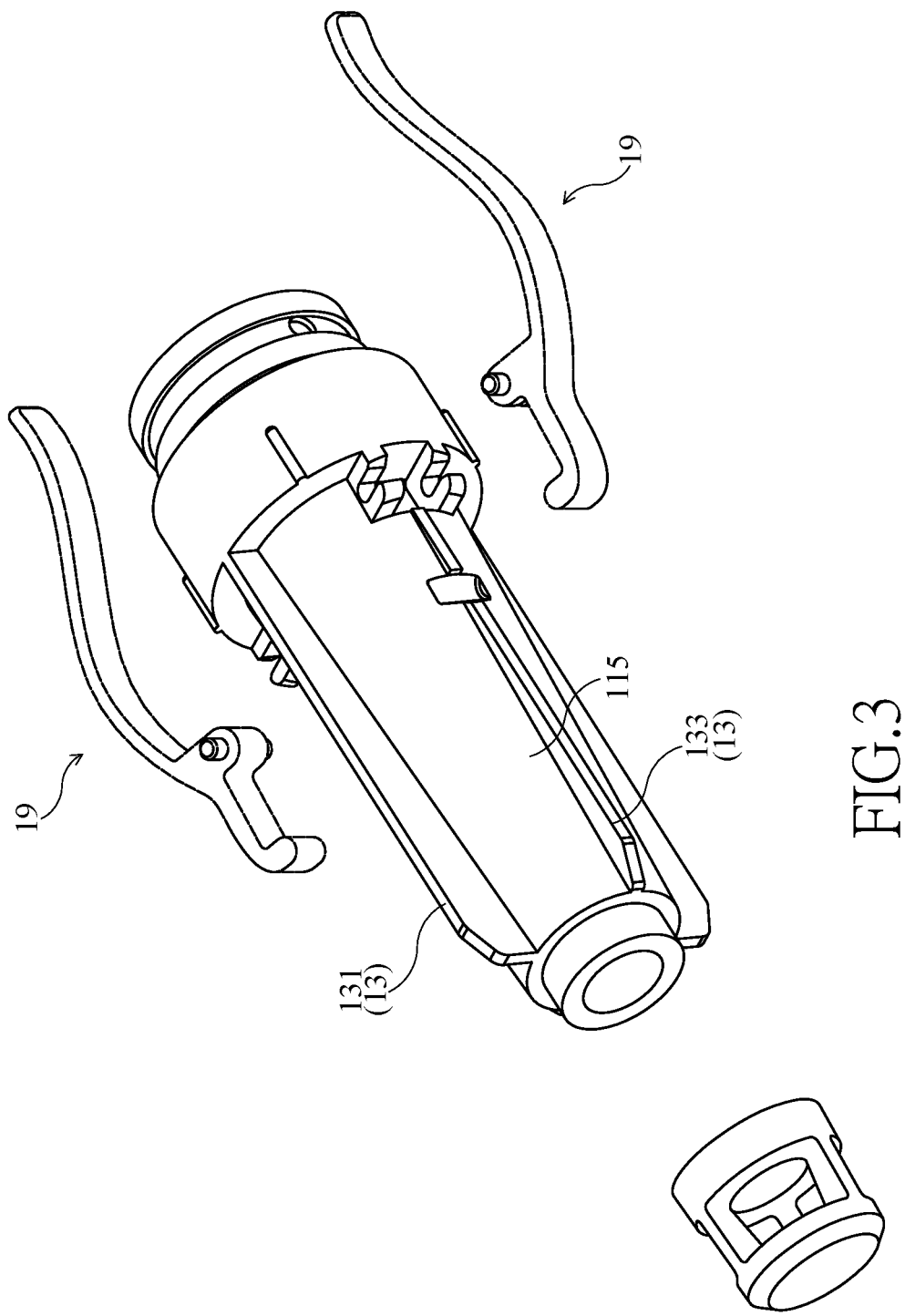
FIG. 3 is an exploded view of an occult blood testing device according to another embodiment of the invention.
Figure 4:
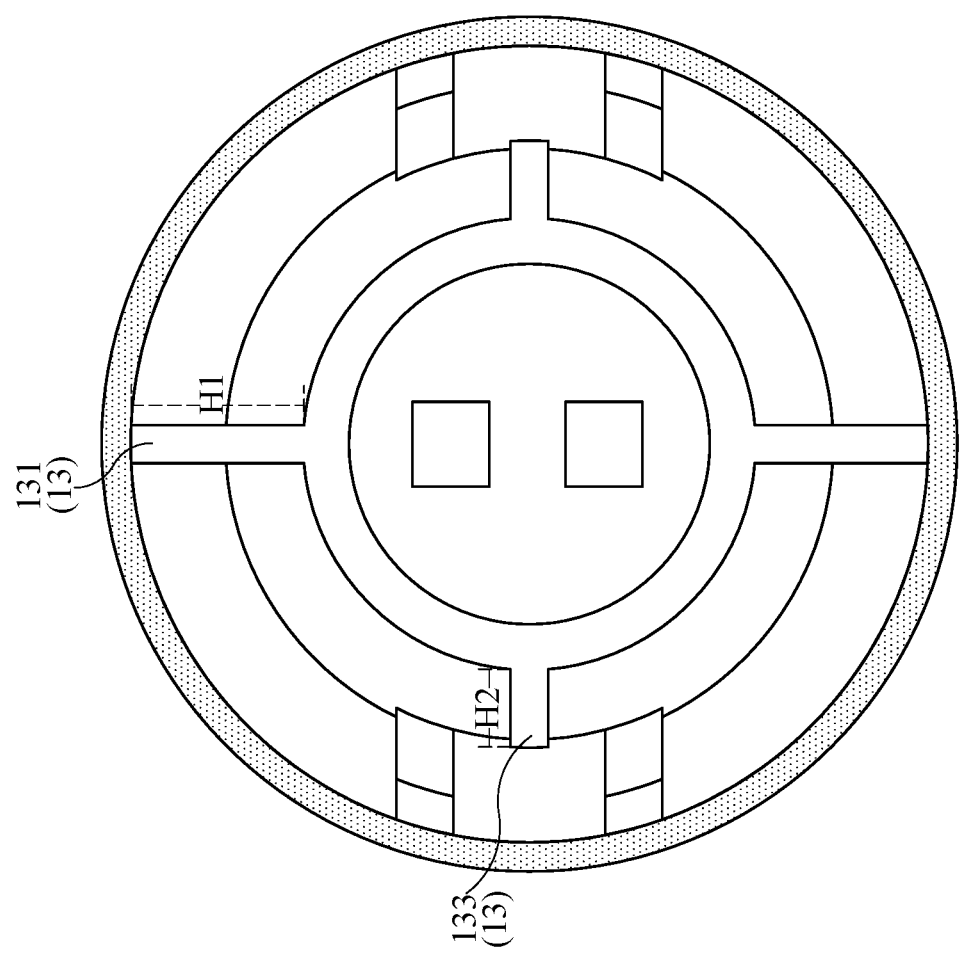
FIG. 4 is a side view, taken from an open end, of an occult blood testing device according to another embodiment of the invention.

The ribs 13 in FIGS. 1 and 2 are of the same size and shape, but in different embodiments, the shape, height and size of each rib 13 can be different from one another. For example, the height of two opposing ribs 13 of the plurality of ribs 13 can be greater than the height of other ribs 13 as shown in FIGS. 3 and 4. In specific, the four ribs 13 include two opposing first ribs 131 and two opposing second ribs 133 and the first ribs 131 and the second ribs 133 are alternately disposed on the outer surface 115 of the main body 11, wherein the height H1 of the first ribs 131 is greater than the height H2 of the second ribs 133.

It is to be noted that the use of four ribs 13 is merely an embodiment of the invention, and that the invention does not limit the number of ribs 13. In fact, at least gap can be form between the filter unit 12 and the outer surface 115 of the main body 11 if the outer surface 115 of the main body 11 has a plurality of ribs 13 of any number disposed thereon, and thus the purpose of expelling gas from the accommodation space 112 of the main body 11 and/or the test space 176 of the probe unit 17 is achieved.

Moreover, a chamfer 132 or a fillet may be disposed at one end of the rib 13 that is closer to the open end 111 of the main body 11 to make it easier for the user to sleeve the filter unit 12 over the main body 11 and the ribs 13.

In one embodiment of the invention, the occult blood testing device 10 further includes a plurality of elastic clips 19, wherein the elastic clips 19 are disposed on the outer surface 115 of the main body 11 for clipping and holding the filter unit 12 that is sleeved over the outer surface 115 of the main body 11.

In particular, each of the elastic clips 19 includes a push portion 191, a clip portion 193, and a rotating axel 195, and the outer surface 115 of the main body 11 includes a plurality of connect recesses 117 disposed thereon, wherein the rotating axel 195 of the elastic clip 19 is disposed/positioned in the connect recess 117 of the main body 11.

The elastic clip 19 is a long strip with an inner surface and an outer surface, wherein the clip portion 193 is disposed on the inner surface of the elastic clip 19 and the push portion 191 is disposed on the outer surface of the elastic clip 19. The push portion 191 is, for example, an arc structure that is curved in a direction from the inner surface to the outer surface of the elastic clip 19, and the clip portion 193 is a structure protruding from the inner surface of the elastic clip 19. When the user presses the push portion 191 of the elastic clip 19, the clip portion 193 is pivoted by the rotating axel 195 acting as an axis to move towards or away from the surface of the main body and thereby clipping or releasing the filter unit 12 between the main body 11 and the elastic clip 19.

When the ribs 13 disposed on the main body 11 have different heights, the connect recesses 117 and the elastic clips 19 are positioned closer or adjacent to the ribs 13 with a lower height. As shown in FIG. 3, the elastic clip 19 is disposed on the second rib 133 which has a lower height so as to clip the filter unit 12 firmly to the outer surface 115 of the main body 11.

It is to be noted that the occult blood testing device 10 having a plurality of elastic clips 19 is merely an embodiment of the invention, and the invention is not limited thereby. In practice, the occult blood testing device 10 may have no elastic clip 19 and connect recess 117, and the filter unit 12 is directly sleeved over the main body 11.

Figure 5:
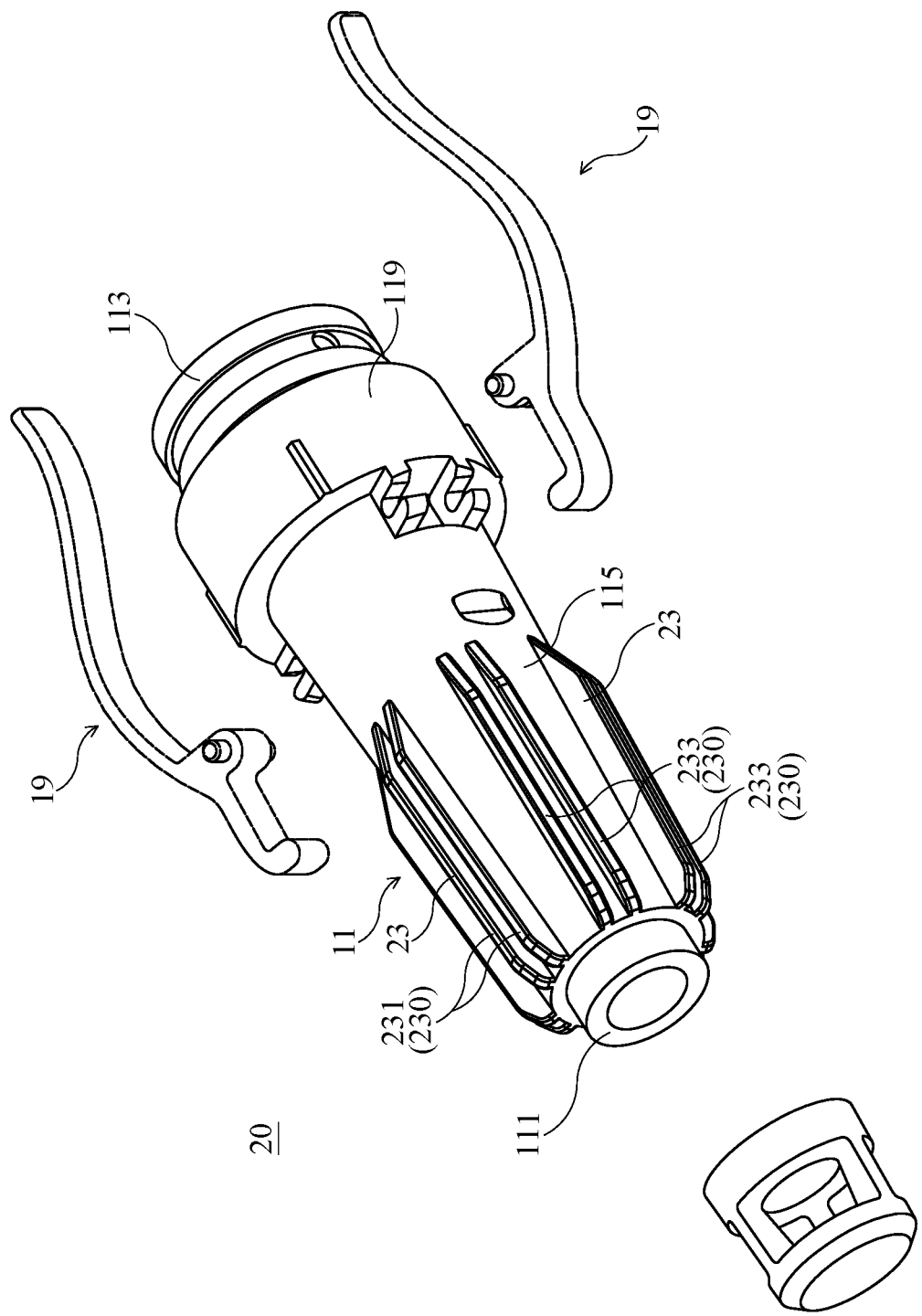
FIG. 5 is an exploded view of an occult blood testing device according to yet another embodiment of the invention.
Figure 6:
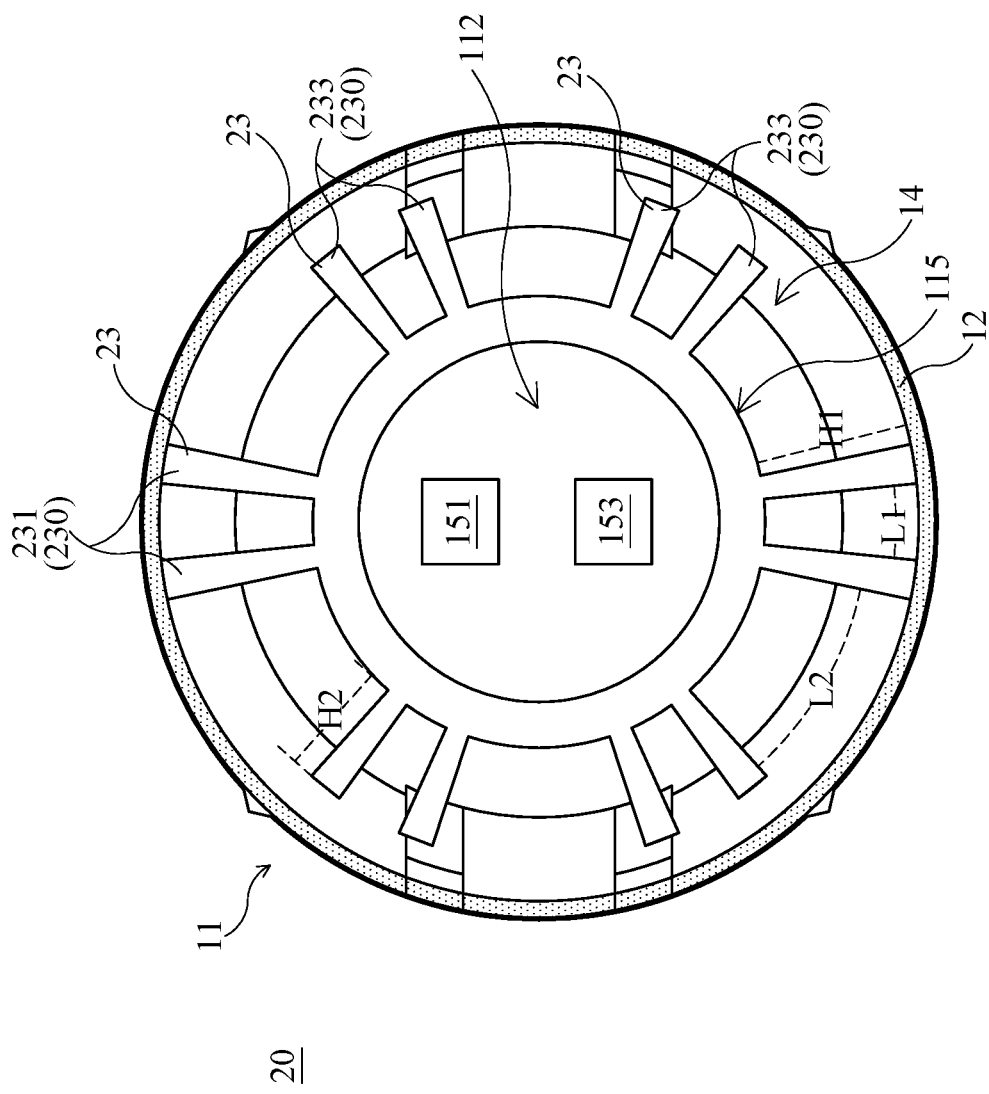
FIG. 6 is a side view, taken from an open end, of an occult blood testing device according to yet another embodiment of the invention.

FIGS. 5 and 6 are, respectively, an exploded view and a side view of an occult blood testing device according to yet another embodiment of the invention. The occult blood testing device 20 includes a main body 11, a plurality of rib sets 230, at least one light emitting unit 151 and at least one light sensing unit 153, wherein the plurality of rib sets 230 are disposed on an outer surface 115 of the main body 11.

Each of the plurality of rib sets 230 includes a plurality of ribs 23, wherein each of the ribs 23 is disposed along a direction from an open end 111 of the main body 11 to a tail end 113 of the main body 11. For example, the rib 23 is disposed on the outer surface 115 of the main body 11 along an axial direction of the main body 11 and protrudes from the outer surface 115 of the main body 11 from a radial direction of the main body 11.

The occult blood testing device 20 of this embodiment is structurally and functionally similar to the occult blood testing device 10 of FIGS. 1 and 2, and the main difference is that in this embodiment, there are a greater number of ribs 23 disposed on the outer surface 115 of the main body 11.

In one embodiment of the invention, the plurality of rib sets 230 are uniformly disposed on the outer surface 115 of the main body 11, wherein each of the rib sets 230 includes two ribs 23. A distance L1 between the two ribs 23 of each rib set 230 is shorter than a distance L2 between two adjacent rib sets 230.

Referring to FIGS. 5 and 6, the number of ribs 23 is twelve, wherein the twelve ribs 23 are grouped into six rib sets 230, and each rib set 230 has two ribs 23. These six rib sets 230 are uniformly disposed on the outer surface 115 of the main body 11.

In another embodiment of the invention, a height H1 of the ribs 23 belonging to two opposing rib sets 230, like the first rib sets 231, of the plurality of rib sets 230 is greater than a height H2 of the ribs 23 belonging to other rib sets 230, like the second rib sets 233.

The occult blood testing device 20 may include a plurality of elastic clips 19 for clipping a filter unit 12 that is sleeved over the outer surface 115 of the main body 11. In one embodiment of the invention, the elastic clips 19 are disposed between two second rib sets 233 that have a lower height so as to hold the filter unit 12 firmly onto the main body 11.

Figure 7:
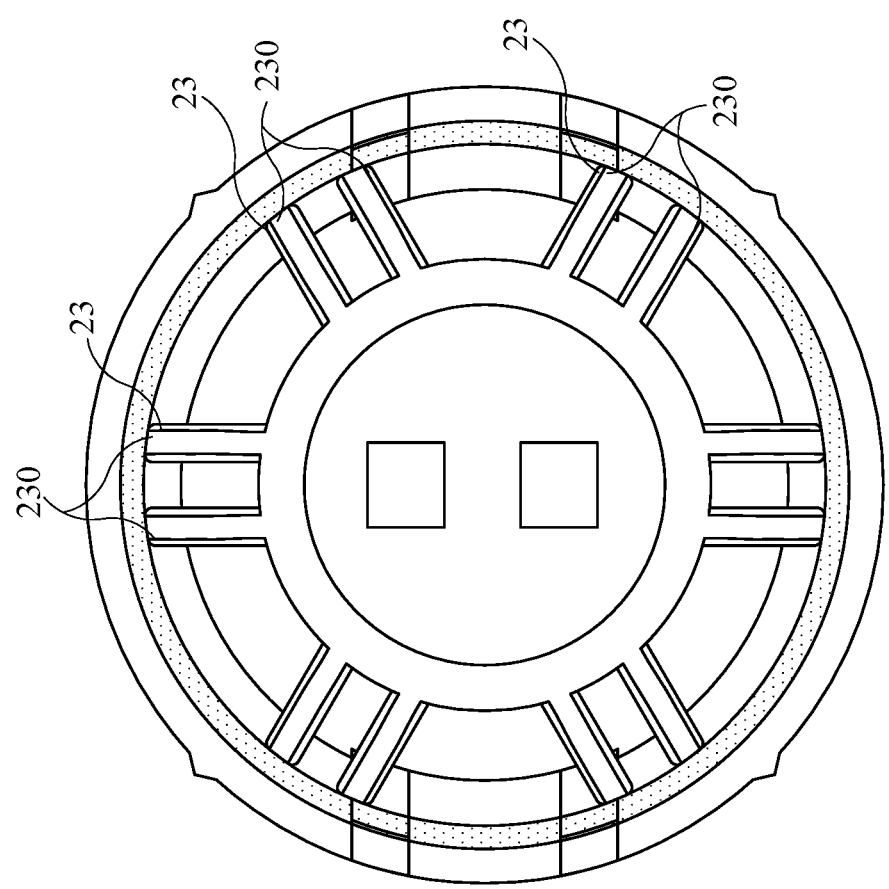
FIG. 7 is a side view, taken from an open end, of an occult blood testing device according to yet another embodiment of the invention.

Each of the ribs 23 shown in FIG. 6 protrudes from the outer surface 115 of the main body 11 in a radial direction of the main body 11, wherein the two ribs 23 in the same rib set 230 are not parallel to each other. In different embodiments, the ribs 23 protrude from the outer surface 115 of the main body 11 but not in the radial direction of the main body 11, wherein the plurality of ribs 23 in the same rib set 230 are parallel to one another. As shown in FIG. 7, an extension line of each rib 23 does not pass the axis of the main body 11, and the two ribs 23 in each rib set 230 are parallel to each other.

It is to be noted that disposing twelve ribs 23, which are grouped into six rib sets 230 with two ribs 23 to each rib set 230, on the outer surface 115 of the main body 11 is merely an embodiment of the invention, and the invention is not limited thereby. In practice, the number of ribs 23 may be greater or less than twelve and the number of ribs 23 in each rib set 230 may be greater than two.

In one embodiment of the invention, a collar 119 is disposed on the outer surface 115 of the main body 11, wherein the collar 119 protrudes from the outer surface 115 of the main body 11 and is near the tail end 113 of the main body 11. In the embodiment of FIGS. 1 and 3, one end of the rib 13 is close to the open end 111 and the other end extends to and comes in contact with the collar 119. In the embodiment of FIG. 5, one end of the rib 23 is close to the open end 111 and the other end does not touch/come in contact with or connect to the collar 119.

The above disclosure is only the preferred embodiment of the present invention, and not used for limiting the scope of the present invention. All equivalent variations and modifications on the basis of shapes, structures, features and spirits described in claims of the present invention should be included in the claims of the present invention.

What is claimed is:

1. An occult blood testing device comprising:
   a main body comprising an open end, a tail end, and an accommodation space, wherein the main body is hollow and the open end is in fluid communication with the accommodation space;
   a plurality of ribs disposed on an outer surface of the main body and along a direction from the open end to the tail end of the main body;
   at least one light emitting unit disposed in the accommodation space of the main body for emitting an incident light beam, wherein the incident light beam is aimed towards a direction of the open end and at a test solution, and the at least one incident light beam that penetrated the test solution forms at least one detection light beam; and
   at least one light sensing unit disposed in the accommodation space of the main body for receiving the at least one detection light beam.

2. The occult blood testing device of claim 1, wherein the ribs are disposed on the outer surface of the main body along an axial direction of the main body and protrude from the outer surface of the main body along a radial direction of the main body.

3. The occult blood testing device of claim 2, wherein any two adjacent ribs of the plurality of ribs have a same included angle.

4. The occult blood testing device of claim 3, wherein a height of two opposing ribs of the plurality of ribs is greater than a height of other ribs.

5. The occult blood testing device of claim 1, further comprising a probe unit that comprises a base, a connect end, a test space, and at least one through hole, wherein the connect end and the through hole are in fluid communication with the test space, the connect end faces the base, and when the connect end is connected to the open end of the main body, the test space is in fluid communication with the accommodation space of the main body.

6. The occult blood testing device of claim 1, further comprising a plurality of elastic clips connected to the main body for clipping a filter unit that is sleeved over the outer surface of the main body.

7. The occult blood testing device of claim 6, wherein a height of two opposing ribs is greater than a height of other ribs, and the elastic clips are adjacent to the ribs that have a lower height.

8. An occult blood testing device comprising:
   a main body comprising an open end, a tail end, and an accommodation space, wherein the main body is hollow and the open end is in fluid communication with the accommodation space;
   a plurality of rib sets disposed on an outer surface of the main body, wherein each of the rib sets comprises a plurality of ribs disposed along a direction from the open end to the tail end of the main body;
   at least one light emitting unit disposed in the accommodation space of the main body for emitting at least one incident light beam, wherein the incident light beam is aimed towards the open end and at a test solution, and the at least one incident light beam that penetrated the test solution forms at least one detection light beam; and
   at least one light sensing unit disposed in the accommodation space of the main body for receiving the at least one detection light beam.

9. The occult blood testing device of claim 8, wherein the ribs are disposed on the outer surface of the main body along an axial direction of the main body and protrude from the outer surface of the main body along a radial direction of the main body.

10. The occult blood testing device of claim 8, wherein the plurality of ribs of the same rib set are parallel to one another.

11. The occult blood testing device of claim 8, wherein a height of the ribs in two opposing rib sets of the plurality of rub sets is greater than a height of the ribs in other rib sets.

12. The occult blood testing device of claim 8, further comprising a plurality of elastic clips connected to the main body for clipping a filter unit that is sleeved over the outer surface of the main body.

13. The occult blood testing device of claim 12, wherein a height of the ribs in two opposing rib sets of the plurality of rib sets is greater than a height of the ribs in other rib sets, and the elastic clips are adjacent to the ribs that have a lower height.

* * * * *